(12) United States Patent
Richey et al.

(10) Patent No.: US 9,393,211 B2
(45) Date of Patent: Jul. 19, 2016

(54) HIGH DRUG LOAD BUPRENORPHINE MICROSPHERES AND METHOD OF PRODUCING SAME

(71) Applicant: Oakwood Laboratories LLC, Oakwood Village, OH (US)

(72) Inventors: Tracy Richey, Kent, OH (US); Bagavathikanun Chithambara Thanoo, Brecksville, OH (US)

(73) Assignee: Oakwood Laboratories LLC, Oakwood Village, OH (US)

( * ) Notice: Subject to any disclaimer, the term of this patent is extended or adjusted under 35 U.S.C. 154(b) by 123 days.

(21) Appl. No.: 13/837,181

(22) Filed: Mar. 15, 2013

(65) Prior Publication Data

US 2014/0271869 A1    Sep. 18, 2014

(51) Int. Cl.
*A61K 9/50* (2006.01)
*A61K 31/485* (2006.01)
*A61K 9/10* (2006.01)

(52) U.S. Cl.
CPC ............... *A61K 9/5031* (2013.01); *A61K 9/10* (2013.01); *A61K 31/485* (2013.01)

(58) Field of Classification Search
CPC ........................... A61K 9/5031; A61K 31/485
See application file for complete search history.

(56) References Cited

U.S. PATENT DOCUMENTS

| | | | |
|---|---|---|---|
| 5,026,556 | A | 6/1991 | Drust et al. |
| 6,495,155 | B1 | 12/2002 | Tice et al. |
| 7,041,320 | B1 | 5/2006 | Nuwayser |
| 7,473,431 | B2 | 1/2009 | Tice et al. |
| 2005/0048115 | A1 | 3/2005 | Mangena et al. |
| 2008/0220070 | A1 | 9/2008 | Fu et al. |
| 2009/0169632 | A1 | 7/2009 | Lu et al. |
| 2012/0021018 | A1 | 1/2012 | Woo et al. |

FOREIGN PATENT DOCUMENTS

| | | |
|---|---|---|
| WO | 2011087496 A1 | 7/2011 |
| WO | 2011154724 A2 | 12/2011 |

OTHER PUBLICATIONS

O'Donnell, Patrick B., and James W. McGinity. "Preparation of microspheres by the solvent evaporation technique." Advanced drug delivery reviews 28.1 (1997): 25-42.*
Bodmeier, R., and J. W. McGinity. "Solvent selection in the preparation of poly (DL-lactide) microspheres prepared by the solvent evaporation method." International journal of pharmaceutics 43.1 (1988): 179-186.*
Mello, N.K., et al.: "Buprenorphine Suppresses Heroin Use by Heroin Addicts", Science, vol. 207, pp. 657-659 Feb. 1980.
Vocci, F., et al.: "Medications Development for the Treatment of Pregnant Addicts and Their Infants", NIDA Res. Monograph 149, 4. pp. 1-15 1995.
Johnson, T., et al.: "A Placebo Controlled Clinical Trial of Buprenorphine as a Treatment for Opioid Dependence", John Hopkins University, Behavioral Pharmacology Research Unit, Drug and Alcohol Dependence 40 pp. 17-25 1995.
Schottenfeld, R.S., et al.: "Buprenorphine vs Methadone Maintenance Treatment for Concurrent Opioid Dependence and Cocaine Abuse", Atch. Gen. Psychiatry, vol. 54, Aug. 1997 pp. 713-720.
Renault, P., et al.: "Narcotic Antagonists: Naltrexone Pharmacochemistry and Sustained-Release Preparation", Nida Res. Monograph Series 28, DHHS (ADM) No. 81-902, Washington, D.C., 1981, pp. 1-22.
Lopatco, OV, et al.: "Opioid Effects and Opioid Withdrawal During a 24 h Dosing interval in Patients Maintained on Buprenorphne", Drug and Alcohol Dependence, 69, 2003 pp. 317-322.
Sigmon, SC, et al.: "An Injection Depot Formulation of Buprenorphine: Extended Biodelivery and Effects", John Hopkins University, Behavioral Pharmacology Research Unit, Addition 101, 2006 pp. 420-432.
Schuh, KJ, et al.: "Pharmacokinetic Comparison of the Buprenorphine Sublingual Liquid and Table", Drug Alcohol Dependence, 56, 1999 pp. 55-60.
Evans, HC, et al.: "Transdermal Buprenorphine", Adis Drug Profile, Drugs, 63, (19) 2003.
Liu, KS, et al.: "Novel Depots of Buprenorphine Prodrugs Have a Long-Acting Natinociceptive Effect", The International Anesthesia Research Society, ANALOG, 102: 2006 pp. 1445-1451.
Kleppner, SR, et al.: "In-vitro and In-Vivo Characterization of a Buprenorphine Delivery System", Journal of Pharmacy and Pharmacology, 58, 2006 pp. 295-302.
Ling, W, et al.: Context: Limitations of existing pharmacological treatments for opioid dependence include low adherence, medication diversion, and emergence of withdrawal systems. JAMA, 304 (14), 2010 pp. 1576-1583. 2010.
Mandal, TK.: "Development of Biodegradable Drug Delivery System to Treat Addiction", Drug Development & Industrial Pharmacy, 25(6), 1999 pp. 773779.
Ravis, WR, et al.: Chapter 39 in Handbook of Controlled Release Technology, Edited by D.L. Wise, Mercer Dekker, Inc. (2000), ISBN: 0-8247-0369-3 pp. 821-836.
Sobel, BFX, et al.: "Open-label Trial of an Injection Depot Formulation of Buprenorphine in Opioid Detoxification", Drug and Alcohol Dependence, 73, 2004 pp. 11-22.
Sigmon, SC., et al.: "Evaluation of an Injection Depot Formulation of Buprenorphine: Placebo Comparison", Society for the Study of Addiction, 99, 2004 pp. 1439-1449.
International Search Report from PCT/US2014/027982 filed Mar. 14, 2014, mailing date of Aug. 19, 2014, pp. 1-7.

\* cited by examiner

*Primary Examiner* — Bethany Barham
*Assistant Examiner* — Peter Anthopolos
(74) *Attorney, Agent, or Firm* — Benesch, Friedlander, Coplan & Aronoff LLP (57) ABSTRACT

A sustained release microsphere formulation with a high drug load may be formed by a continuous oil-in-water emulsion process by combining an organic dispersed phase with an aqueous continuous phase. The dispersed phase may include an encapsulating polymer, a primary solvent, such as dichloromethane, a pharmaceutically effective amount of an active agent having a solubility relative to the dispersed phase, and a co-solvent, such as benzyl alcohol, which is capable of increasing the solubility of the active agent relative to the dispersed phase. The continuous phase may include an aqueous solution of polyvinyl alcohol and water.

9 Claims, 7 Drawing Sheets

HIGH DRUG LOAD BUPRENORPHINE MICROSPHERES AND METHOD OF PRODUCING SAME

FIELD OF INVENTION

The present disclosure relates to a buprenorphine microsphere formulation with an improved or increased drug load and a low initial burst release, and a method of producing the same. Specifically, the disclosure relates to a method of efficiently manufacturing a sustained released microsphere with a high drug load by improving the solubility of the active agent, such as buprenorphine, relative to the dispersed phase of the microsphere formation process and preparing buprenorphine microsphere formulations with varying durations of drug release.

BACKGROUND

Buprenorphine is a known treatment for narcotic addiction and may be used to treat other conditions, such as psychiatric disorders, depression, and schizophrenia. Generally, buprenorphine is administered with a sublingual tablet (commercially available as Suboxone) to treat addiction. However, long term maintenance treatment through this route is problematic as it creates withdrawal symptoms due to the steep rise and drop of the drug concentrations in plasma after each dose. Patient compliance and the potential for abuse are also drawbacks for this method of treatment.

Other known delivery methods of buprenorphine include a transdermal patch, sesame oil based formulations, biodegradable and non-biodegradable implants—which can be painful to administer as they require local anesthesia at the implant site. A sustained release injectable microsphere formulation would maintain a steady plasma concentration, preventing withdrawal symptoms.

Injectable polymer solutions containing buprenorphine have been developed to provide sustained release buprenorphine. Upon injection, the solvent diffuses away from the injection site, leaving the buprenorphine containing polymer matrix to release the drug at a controlled rate. However, the solvents utilized, such as N-methyl pyrolidone, in this system are toxic in view of the International Conference on Harmonisation of Technical Requirements for Registration of Pharmaceuticals for Human Use (ICH) and the U.S. Pharmacopeial Convention.

While several methods have been used to achieve a sustained release injectable formulation, the microspheres either had a drug load that was too low to be commercially viable— less than about 2%—were produced with an additional polymer coating, creating manufacturing difficulties, included toxic solvents, or did not provide the desired length of sustained release. It would be desirable to produce a commercially acceptable injectable sustained release microsphere formulation that has both a high drug load and a low initial burst release.

SUMMARY OF THE INVENTION

A sustained release microsphere formulation having a high buprenorphine drug load includes a dispersed phase comprising an encapsulating polymer, a primary solvent, a pharmaceutically effective amount of buprenorphine having a solubility relative to the dispersed phase, and a co-solvent capable of increasing the solubility of the buprenorphine relative to the dispersed phase and a continuous phase comprising an aqueous solution, wherein the dispersed phase may be mixed with the continuous phase to form the microsphere formulation.

In one embodiment, the encapsulating polymer may be selected from the group consisting of poly (D,L-lactide-co-glycolide) and poly(L-lactide) and have an inherent viscosity of about 0.18 $\eta_{inh}$ dL/g to about 0.54 $\eta_{inh}$ dL/g. The continuous phase may include an aqueous solution of water and polyvinyl alcohol.

In another embodiment, the formulation has an initial in-vivo burst release of not more than three times the highest concentration observed during the sustained portion of the buprenorphine release and in another embodiment, not higher than two times the highest concentration observed during the sustained portion of the buprenorphine release.

The co-solvent may be selected from benzyl alcohol, dimethyl sulfoxide, dimethyl formamide, dimethyl acetamide, acetonitrile, ethanol, N-methyl pyrolidone, and ethyl acetate and the buprenorphine may be a free base form of buprenorphine, a salt form of buprenorphine, or a pharmaceutically acceptable mixture thereof.

In one embodiment, the buprenorphine drug load of the formulation is about 15% by weight of the microspheres to about 50% by weight of the microspheres and the co-solvent may be present in an amount of up to 50% by weight of the dispersed phase and is capable of increasing the solubility of the buprenorphine relative to the dispersed phase to about 0.1 g/g to about 0.3 g/g.

In another embodiment, a sustained release microsphere formulation for injection into a patient includes a dispersed phase comprising a poly (D,L-lactide-co-glycolide) polymer with an inherent viscosity of about 0.34 $\eta_{inh}$ dL/g, at least one solvent, and a pharmaceutically effective amount of buprenorphine and a continuous phase comprising an aqueous solution; wherein the dispersed phase may be mixed with the continuous phase to form the microsphere formulation. In this embodiment, the amount of buprenorphine is substantially released from the microsphere formulation in about one month, but less than two months, after it is injected into the patient and the formulation has a drug load of about 35% to about 55% and a mean particle size of about 25 µm to about 45 µm.

In another embodiment, a sustained release microsphere formulation for injection into a patient includes a dispersed phase comprising a hydrophobic poly (D,L-lactide-co-glycolide) polymer with an inherent viscosity of about 0.20 ηinh dL/g, at least one solvent, and a pharmaceutically effective amount of buprenorphine and a continuous phase comprising an aqueous solution; wherein the dispersed phase may be mixed with the continuous phase to form the microsphere formulation. In this embodiment, the amount of buprenorphine is substantially released from the microsphere formulation in about two months, but less than three months, after it is injected into the patient and the formulation has a drug load of about 30% to about 45% and a mean particle size of about 25 µm to about 45 µm.

In another embodiment, a sustained release microsphere formulation for injection into a patient includes a dispersed phase comprising a poly (D,L-lactide-co-glycolide) polymer with a ratio of lactic acid to glycolic acid of between about 50:50 to about 100:0, at least one solvent, and a pharmaceutically effective amount of buprenorphine and a continuous phase comprising an aqueous solution; wherein the dispersed phase may be mixed with the continuous phase to form the microsphere formulation. In this embodiment, the amount of buprenorphine is substantially released from the microsphere formulation over three months, but less than nine months, after it is injected into the patient and the formulation has a drug load of about 30% to about 50% and a mean particle size of about 20 μm to about 45 μm.

BRIEF DESCRIPTION OF DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

DETAILED DESCRIPTION

A sustained release, injectable buprenorphine microsphere formulation, and a method of producing the same, having a drug load of at least about 20% active agent by weight of the microsphere is provided.

In one embodiment, the formulation may also have a low or steady state initial burst release. The microsphere formulation may be used to treat addiction to narcotic agents, although it should be appreciated that the microsphere formulation may be used for any suitable purpose, such as pain management. The microsphere formulation may be formed by a continuous oil in water (O/W) emulsion process that includes providing an organic dispersed phase including at least one encapsulating polymer, a primary solvent, an active agent such as buprenorphine, or a salt thereof, and a co-solvent capable of improving the solubility of the active agent in the dispersed phase, and providing an aqueous continuous phase.

In addition to having a drug load of about 20%, and in some cases up to about 50%, the microsphere formulations have a drug encapsulation efficiency greater than 80%, and in some cases greater than about 90%. The average particle size of the microspheres in the formulations are about 20 micron to about 60 micron, which allows for the use of smaller needles for injection. For example, the microsphere formulation may be injected into a patient using a syringe with a 25 gauge needle or smaller.

In one embodiment, the dispersed phase may include a biodegradable encapsulating polymer, such as poly (D,L-lactide-co-glycolide) (hereinafter "PLGA") or poly(L-lactide) (hereinafter "PLA"), although it is contemplated that other suitable biodegradable polymers may be used, a primary solvent, such as dichloromethane (DCM), and buprenorphine or a salt thereof. The encapsulating polymer may be hydrophobic or hydrophilic. In one embodiment, the encapsulating polymer is hydrophobic. In another embodiment, the encapsulating polymer has an inherent viscosity of about 0.18 $\eta_{inh}$ dL/g to about 0.54 $\eta_{inh}$ dL/g, however it should be appreciated that polymers with other suitable inherent viscosities may be used.

The dispersed phase may also include up to about 50% by weight of a co-solvent capable of increasing the solubility of the active agent in the dispersed phase. In one embodiment, the co-solvent may be benzyl alcohol (BzOH), dimethyl sulfoxide (DMSO), dimethyl formamide (DMF), dimethyl acetamide (DMAc), acetonitrile (ACN), ethanol (EtOH), N-methyl pyrolidone (NMP), ethyl acetate (EA), or any other solvent that increases the solubility of buprenorphine in the dispersed phase containing dichloromethane. In another embodiment, the co-solvent is benzyl alcohol or dimethyl sulfoxide, and in yet another embodiment, the co-solvent is benzyl alcohol.

Example 1

Solubility of Buprenorphine

The solubility of buprenorphine in various solvents was determined by adding 0.5 g of buprenorphine into a 20.0 mL glass vial and dissolving it in increasing volumes of solvent until solubility was achieved by visual observation. DCM was used as the main solvent and BzOH as the co-solvent. An equal amount of D,L-PLA was then added to each vial to confirm that the solubility of the drug in the solvent system was not compromised by the introduction of the polymer. As shown below in Table 1, the addition of BzOH to the DCM increased the solubility of buprenorphine by about six (6) fold.

TABLE 1

| Solvent System | Co-solvent (% added by volume) | Buprenorphine Solubility (g/g) | Buprenorphine Solubility (g/g) in presence of equal amount of PLA |
|---|---|---|---|
| DCM | None | 0.022 | 0.022 |
|  | Benzyl alcohol (33%) | 0.125 | 0.125 |

Example 2

Preparation of Buprenorphine Microspheres

The buprenorphine microsphere formulation may generally be prepared using a continuous W/O emulsification/solvent extraction procedure. Generally, a dispersed phase is provided by dissolving a polymer in a primary solvent, such as DCM, and a co-solvent capable of increasing the solubility of buprenorphine, such as BzOH. Buprenorphine is then added to the polymer solution and mixed until dissolved. The dispersed phase is then filtered using a 0.2 micron sterilizing PTFE or PVDF membrane filter (such as EMFLON, commercially available from Pall) and pumped into a homogenizer, such as an in-line Silverson Homogenizer (commercially available from Silverson Machines, Waterside UK), at a defined flow rate.

Simultaneously, a continuous phase including an aqueous solution containing a surfactant, such as polyvinyl alcohol (PVA), is also pumped into the homogenizer at a defined flow rate. The speed of the homogenizer is generally fixed to achieve a desired microsphere size distribution. This continuous microsphere process is described in U.S. Pat. No. 5,945,126, and is incorporated by reference herein in its entirety.

The formed or forming microspheres exit the homogenizer and enter a solvent removal vessel (SRV). Water is added to the SRV during microsphere formation in order to minimize the solvent level in the aqueous medium. The resulting suspension is mixed in the SRV during the microsphere formation period. After the dispersed phase has been exhausted, the continuous and water flow rates are stopped, and the washing steps are initiated. Solvent removal is achieved using water washing and a hollow fiber filter (commercially available as HFF from GE Healthcare). This system previously is disclosed in U.S. Pat. No. 6,270,802, which is incorporated by reference herein in its entirety.

The washing steps begin by washing the microsphere suspension with room temperature water, followed by washing the suspension with hot water (about 40° C.) for approximately 60 minutes before cooling the suspension back down to room temperature.

The washed microspheres are then collected and freeze-dried overnight in a lyophilizer (Virtis) to remove all of the moisture. The resulting microspheres are a free-flowing off-white bulk powder.

In use, the microspheres may be suspended in a diluent for administration (injection). The diluent may generally contain a thickening agent, a tonicity agent, and a surfactant. The thickening agent may include carboxymethyl cellulose-sodium (CMC-Na) or other suitable compounds. An appropriate viscosity grade and suitable concentration of CMC-Na may be selected so that the viscosity of the diluent is 3 cps or higher. Generally, a viscosity of about 10 cps is suitable, however a higher viscosity diluent may be preferred for larger microspheres in order to minimize the settling of microspheres in the suspension.

Uniform microsphere suspension without particle settling will result in a consistent delivered dose during drug administration by injection. In order to have a tonicity of the diluent closer to the biological system, about 290 milliosmole (mOsm), solutes such as mannitol, sodium chloride, or any other acceptable salt may be used. The diluent may also contain a buffer salt to maintain the pH of the composition. Typically the pH is maintained around neutral (pH 7). If the microsphere formulation is hydrophobic, surfactants such as Polysorbates-80 or Span may be used to provide wettability of the microsphere formulation. In one embodiment, small quantities of the surfactant, about 1 mg/mL, may be used to provide sufficient wettability of the microspheres.

In one embodiment, the diluent may be provided in a separate vial if the microsphere formulation vial contains microspheres only. In yet another embodiment, the components of the diluent may be provided along with the microsphere. For this type of packaging configuration, sterile water for injection may be used as the reconstitution fluid.

Example 3

Effect of Co-solvents

Generally, the solvent in the dispersed phase has to be extracted in order to form microspheres. Without the use of the co-solvent, the amount of DCM required to keep buprenorphine solubilized in dispersed phase is very high, especially in order to achieve high target load microspheres. Therefore, the amount of continuous phase required will be very high, as compared to a microsphere formation made with a co-solvent. For example, as discussed above, the solubility of buprenorphine in dichloromethane is 0.022 g/g. By using a 2:1 mixture of DCM:BzOH, the solubility of buprenorphine increased about 6 fold to 0.125 g/g. Thus, incorporation of a co-solvent reduces the amount of continuous phase needed by about 6 fold and allows for larger batch sizes to be produced while keeping the volumes of the continuous and dispersed phases lower.

In this example two batches of microspheres were prepared. For the first batch, a 9.1 wt % polymer solution was prepared by dissolving 2.5 g of a 50:50 PLGA polymer (commercially available as RG503H from Evonik, with an inherent viscosity of 0.34 dL/g) in 25.0 g of a 2:1 mixture of DCM (commercially available from Spectrum Chemicals) and BzOH (commercially available from J.T. Baker). Next, 2.5 g of buprenorphine (alkaloid base form commercially available from Johnson Mathey in West Deptford, N.J.) was added to the polymer solution and dissolved to obtain the dispersed phase.

For the second batch, a 2.0 wt % polymer solution was prepared by dissolving 2.5 g of 50:50 PLGA (commercially available as RG503H, from Evonik, with an inherent viscosity of 0.34 dL/g) in 120.0 g of DCM. Next, 2.5 g of buprenorphine was dissolved in the polymer solution to obtain the dispersed phase.

For each batch, a 0.35 wt % polyvinyl alcohol (PVA) solution was prepared for the continuous phase by adding PVA to room temperature water and heating and mixing the continuous phase above 70° C. for one hour. After cooling the continuous phase, it was filtered using a 0.2 μm hydrophilic PVDF filter (such as a Durapore membrane, commercially available from Millipore).

The microspheres were prepared using the general method previously described in Example 2. The speed of the homogenizer was set at 1500 rpm for the first batch, while 2000 rpm was used for the second batch. The change in homogenizer speeds was necessary because of the difference in viscosities of the two dispersed phases. In order to achieve solubility, much more solvent was required for the second batch, about 120.0 g DCM, compared to the first batch, about 25.0 g DCM/BzOH, thus making the viscosity of the second batch lower than that of the first. Because the viscosity of the dispersed phase will affect the final size and size distribution of the microsphere; a higher homogenizer speed was utilized for the first batch in an attempt to maintain similar particle sizes.

The formed or forming microspheres of both batches exited the homogenizer and entered into a glass vessel at a rate of 2.0 liters per minute. In addition, water was added to the glass vessel at a rate of 2.0 liters per minute during microsphere formation. The batches were mixed in the vessel during the microsphere formation period. After the dispersed phases of each batch were exhausted, the continuous phase and water flow rates were stopped.

For the first batch, the glass vessel was also the solvent removal vessel, and the washing steps were initiated. For the second batch, a large volume of suspension was manufactured; therefore, it was necessary to concentrate the suspension into a smaller solvent removal vessel before the washing steps were started. This was accomplished by using a hollow fiber filter (commercially available as HFF from GE Healthcare). 15 liters of suspension was reduced to 4 liters by this procedure.

The preparation parameters of the buprenorphine microspheres, as well as the measured drug load and size distribution of the dried microspheres are summarized in Table 2.

TABLE 2

| Parameters | Batch Number | |
|---|---|---|
| | 1 | 2 |
| Buprenorphine | Free-base | Free-base |
| Dispersed Phase Solvent 1 | DCM | DCM |
| Dispersed Phase Solvent 2 | BzOH | None |
| Co-Solvent Ratio (DCM:BzOH) | 2:1 | N/A |
| Mixer Speed (rpm) | 2000 | 1500 |
| Target Drug load (wt %) | 50 | 50 |
| Dispersed Phase Flow Rate (ml/min) | 25 | 25 |
| Continuous Phase Flow Rate (mL/min) | 2000 | 2000 |
| Water Dilution Rate (mL/min) | 2000 | 2000 |
| Drug Load (wt %) | 46.9 | 48.6 |
| Drug Encapsulation Efficiency (%) | 94 | 97 |
| Particle Size (µm) 10% CVF | 13.0 | 21.1 |
| 25% CVF | 23.2 | 32.1 |
| 50% CVF | 33.4 | 45.9 |
| 75% CVF | 44.3 | 62.6 |
| 90% CVF | 56.7 | 83.1 |

Figure 1:
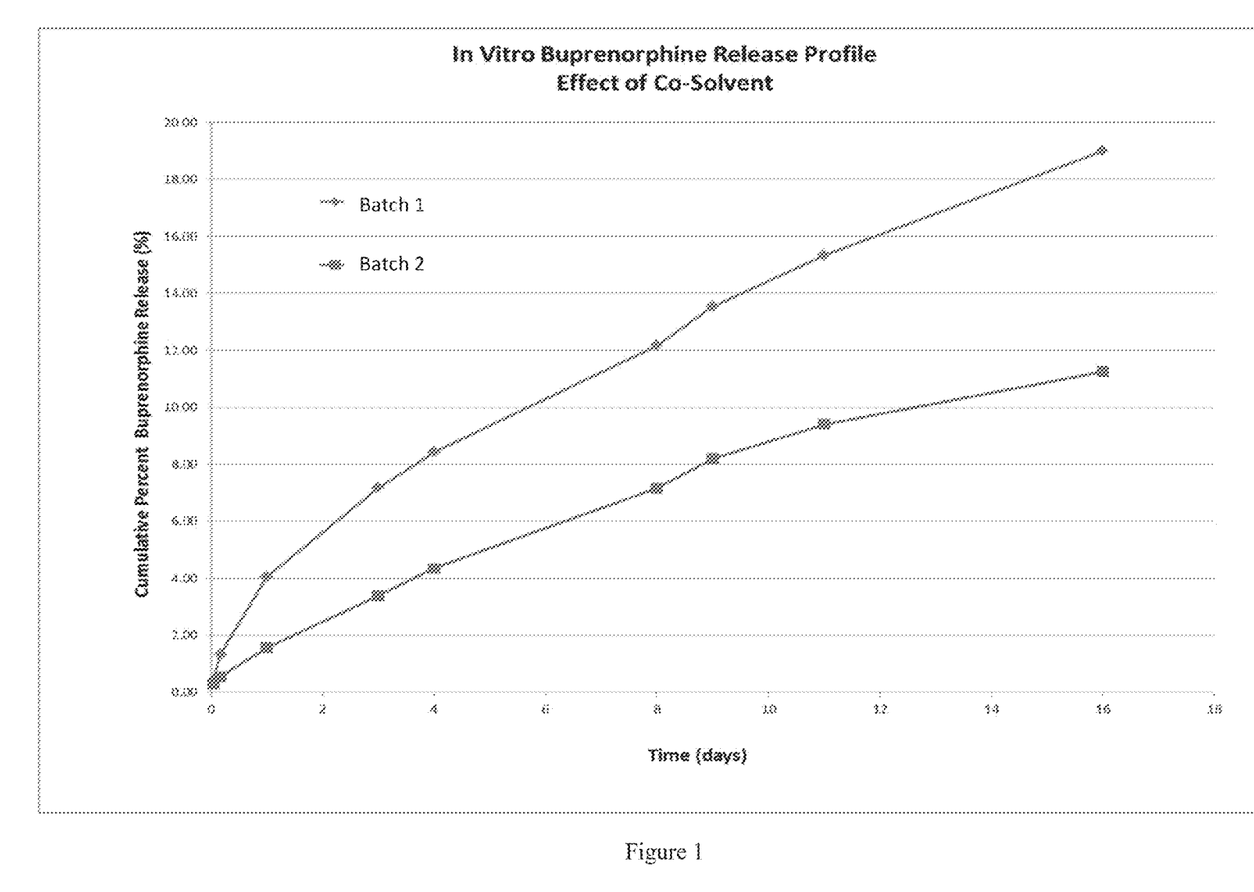
FIG. 1 is a graph of the in vitro buprenorphine release profile over time for two batches of buprenorphine microspheres formed with and without a co-solvent.

The use of a single solvent or co-solvent had little effect on the drug load of the prepared microspheres, with both batches achieving a high encapsulation efficiency. The batch prepared with DCM alone had a slightly larger average particle size due to the lower mixing speed of 1500 rpm. Notably, the major difference between using a co-solvent such as benzyl alcohol was the improvement in manufacturing and scalability. The first batch required far less solvents in the dispersed phase and consequently much less continuous phase solution and less time for manufacturing. Moreover, microspheres produced with DCM alone showed a slower in-vitro release rate compared with the batch prepared with the DCM/BzOH co-solvent system, as shown in FIG. 1.

Example 4

Free Base Buprenorphine Versus Buprenorphine HCL

Buprenorphine can exist in a free-base (i.e. alkaloid) form or a salt form (ex. Hydrochloride salt). Selection of buprenorphine drug as free base form or as salt form affects the drug encapsulation and drug release duration. Buprenorphine hydrochloride is more soluble in water, therefore encapsulation by O/W emulsification could be challenging especially with high target drug load. By selecting an appropriate solvent system, buprenorphine hydrochloride microspheres were produced with 19% drug load and 76% encapsulation efficiency as shown in the example. Buprenorphine free base has less water solubility and microspheres with drug load as high as 47% were achieved with 94% drug encapsulation efficiency.

In this example, buprenorphine was encapsulated into PLGA microspheres in both the free-base and the salt form. In first and second batches, a 20 wt % polymer solution was prepared by dissolving 3.75 g of 50:50 PLGA (RG502H, commercially available from Evonik with an inherent viscosity of 0.19 dL/g) in 15.0 g of a 2:1 mixture of DCM and BzOH. For the first batch, 1.25 g of salt form of buprenorphine was dissolved in the polymer solution to form the dispersed phase. For the second batch, 1.25 g of the free form of buprenorphine was dissolved in the polymer solution to form the dispersed phase.

For each batch, a 0.35 wt % polyvinyl alcohol (PVA) continuous phase was prepared by the adding PVA to room temperature water and heating and mixing the mixture above 70° C. for one hour. After cooling the continuous phase, it was filtered using a 0.2 µm hydrophilic PVDF filter (such as the Durapore membrane commercially available from Millipore). The microsphere batches were prepared using the general method previously described in Example 2. The process parameters for these two batches are given in Table 3, as well as the measured drug load and size distribution of the dried microspheres.

TABLE 3

| | Batch Number | |
|---|---|---|
| | 1 | 2 |
| Buprenorphine | Salt form (HCL) | Free-base |
| Mixer Speed (rpm) | 2000 | 2000 |
| Target Drug load (wt %) | 25 | 25 |
| Dispersed Phase Flow Rate (mL/min) | 25 | 25 |
| Continuous Phase Flow Rate (mL/min) | 2000 | 2000 |
| Water Dilution Rate (mL/min) | 2000 | 2000 |
| Drug Load (wt/wt %) | 19 | 23 |
| Drug encapsulation efficiency (%) | 76 | 92 |
| Particle Size (µm) 10% CVF | 19.1 | 9.5 |
| 25% CVF | 34.0 | 26.7 |
| 50% CVF | 55.5 | 47.4 |
| 75% CVF | 77.7 | 63.4 |
| 90% CVF | 102.3 | 78.3 |

As shown in Table 3, the final drug load for the batch prepared with the salt form was slightly lower than that prepared from the free base. In addition, its particle size was slightly larger.

Figure 2:
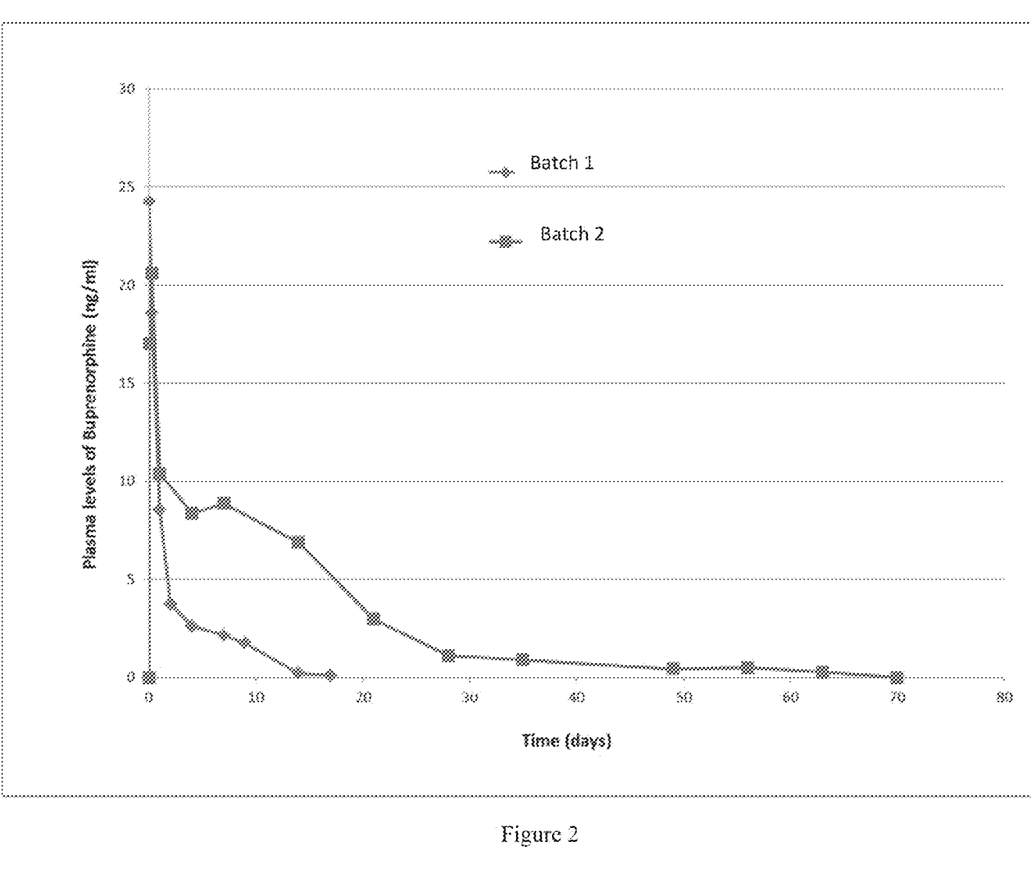
FIG. 2 is a graph of the plasma buprenorphine concentrations in rats given a single administration of microspheres including 3.0 mg buprenorphine/kg of buprenorphine HCL or 15.0 mg buprenorphine/kg of buprenorphine free-base.

The pharmacokinetics of a single administration in rats (3 mg buprenorphine/kg for buprenorphine-HCL and 15 mg buprenorphine/kg for buprenorphine free-base) was measured using the microspheres in Example 3. Plasma buprenorphine concentrations were measured by liquid chromatography-mass spectrophotometry (LC-MS). As shown in FIG. 2, the plasma levels for the batch prepared with the free base form had a much longer duration than that prepared with the salt form, using the same polymer matrix, and similar drug loads. The burst release for both batches was similar.

Example 5

Effect of Target Load

Buprenorphine (free-base form) was encapsulated into PLGA microspheres using varying target drug loads. For the first batch with 25 wt % target drug load, a 17.6 wt % polymer solution was prepared by dissolving 3.75 g of 50:50 PLGA (RG503H commercially available from Evonik with an inherent viscosity of 0.34 dL/g) in 17.5 g of a 2:1 mixture of DCM and BzOH. Next, 1.25 g of buprenorphine was added to the polymer solution and dissolved to form the dispersed phase.

For the second batch with a 50 wt % target drug load, a 9.1 wt % polymer solution was prepared by dissolving 2.5 g of 50:50 PLGA (RG503H commercially available from Evonik with an inherent viscosity of 0.34 dL/g) in 25.0 g of a 2:1 mixture of DCM and BzOH. Next, 2.5 g of buprenorphine was added to the polymer solution and dissolved to obtain the dispersed phase.

For each batch, a 0.35 wt % PVA continuous phase (CP) is prepared by adding PVA to room temperature water and heating and mixing the continuous phase above 70° C. for one hour. After cooling the continuous phase, it was filtered using a 0.2 μm hydrophilic PVDF filter (such as the Durapore membrane from Millipore). The microspheres were prepared using the general method previously described in Example 2. The process parameters for the two batches are given in Table 4, as well as the measured drug load and size distribution of the dried microspheres.

TABLE 4

|  |  | Batch Number | |
|---|---|---|---|
|  |  | 1 | 2 |
| Buprenorphine |  | Free-base | Free-base |
| Mixer Speed (rpm) |  | 2500 | 2000 |
| Target Drug load (wt %) |  | 25 | 50 |
| Dispersed Phase Flow Rate (mL/min) |  | 25 | 25 |
| Continuous Phase Flow Rate (mL/min) |  | 2000 | 2000 |
| Water Dilution Rate (mL/min) |  | 2000 | 2000 |
| Drug Load (wt %) |  | 23.8 | 46.9 |
| Drug encapsulation efficiency (%) |  | 95 | 94 |
| Particle Size | 10% CVF | 16.7 | 13.0 |
| (μm) | 25% CVF | 34.4 | 23.2 |
|  | 50% CVF | 56.3 | 33.4 |
|  | 75% CVF | 82.4 | 44.3 |
|  | 90% CVF | 143.3 | 56.7 |

The final drug loads of the two batches (23.8 wt % for the target load of 25 wt % and 46.9 wt % for the target load of 50 wt %) exhibited a high rate of encapsulation efficiency (i.e. >94%). The size and size distribution of the batch prepared with a high target load were smaller than that formulated with the lower target load. This is due to the lower viscosity of the dispersed phase when a lower polymer concentration used. In order to dissolve the larger amount of buprenorphine in the higher target load formulation, it was necessary to increase the amount of solvents used.

Figure 3:
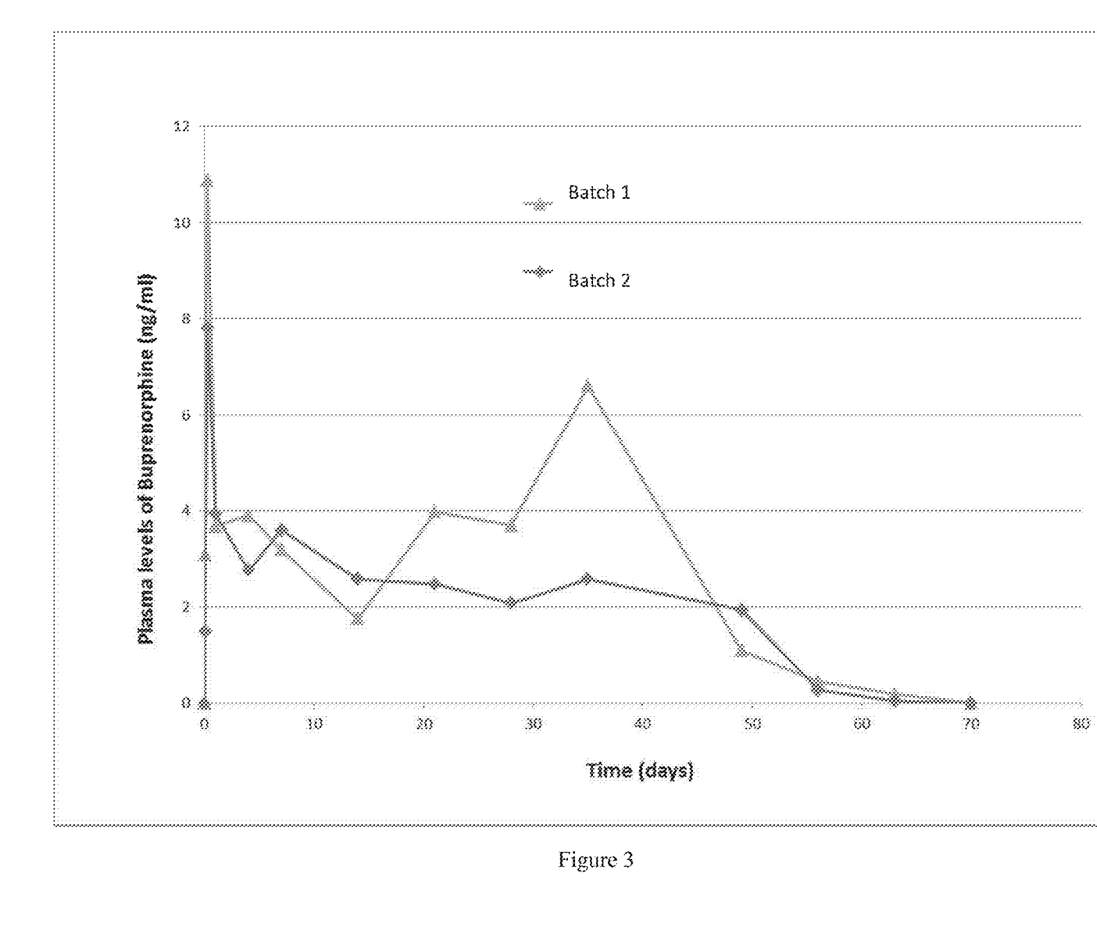
FIG. 3 is a graph of the plasma buprenorphine concentrations in rats given a single administration of microspheres including 15.0 mg buprenorphine/kg and a target drug load of 25% and 50%, respectively.

Pharmacokinetics of a single administration of both formulations in rats (15 mg buprenorphine/kg) was measured using the prepared microspheres. Plasma buprenorphine concentrations were measured by LC-MS. As shown in FIG. 3, both microsphere formulations displayed similar release durations of 50 to 60 days. The microspheres with a higher drug load, batch number 2, exhibited continuous release after a moderate burst, while the microspheres with the lower drug load, batch number 1, showed initial burst followed by a distinct polymer degradation phase release with maximum release around 35 days. Moreover, the plasma levels for batch 2 released substantially all of the buprenorphine over a period of more than one month, but less than two months. Buprenorphine is considered to be "substantially released" when the formulation is no longer capable of producing therapeutic levels of drug in the patient.

Example 6

Effect of Polymer Molecular Weight (Inherent Viscosity)

Buprenorphine (free-base form) was encapsulated into PLGA microspheres using polymers with varying molecular weights. The molecular weight of the polymer may be described by its inherent viscosity ($\eta_{inh}$ dL/g). To prepare a first batch with a lower polymer molecular weight, a 20 wt % polymer solution was prepared by dissolving 3.75 g of 50:50 PLGA (RG502H commercially available from Evonik with an inherent viscosity of 0.19 dL/g) in 15 g of a 2:1 mixture of DCM and BzOH. Next, 1.25 g of was buprenorphine was added to the polymer solution and dissolved to form the dispersed phase.

To prepare second batch with a higher polymer molecular weight, a 17.6 wt % polymer solution was prepared by dissolving 3.75 g of 50:50 PLGA (RG503H commercially available from Evonik with inherent viscosity of 0.34 dL/g) in 17.5 g of a 2:1 mixture of DCM and BzOH. Next, 1.25 g of was buprenorphine was added to the polymer solution and dissolved to obtain the dispersed phase.

For each batch, a 0.35 wt % PVA continuous phase was prepared by adding the PVA to room temperature water and heating and mixing the solution above 70° C. for one hour. After cooling the continuous phase, it was filtered using a 0.2 μm hydrophilic PVDF filter (such as the Durapore membrane from Millipore). The microspheres were prepared using the general method previously described in Example 2. The process parameters for these two batches are given in Table 5, as well as the measured drug load and size distribution of the dried microspheres.

TABLE 5

|  |  | Batch Number | |
|---|---|---|---|
|  |  | 1 | 2 |
| Buprenorphine |  | Free-base | Free-base |
| Polymer $\eta_{inh}$ (dL/g) |  | 0.19 | 0.34 |
| Mixer Speed (rpm) |  | 2000 | 2500 |
| Target Drug load (wt %) |  | 25 | 25 |
| Dispersed Phase Flow Rate (mL/min) |  | 25 | 25 |
| Continuous Phase Flow Rate (mL/min) |  | 2000 | 2000 |
| Water Dilution Rate (mL/min) |  | 2000 | 2000 |
| Drug Load (wt %) |  | 23.1 | 23.8 |
| Drug encapsulation efficiency, % |  | 92.4 | 95.2 |
| Particle Size, | 10% CVF | 9.5 | 16.7 |
| μm | 25% CVF | 26.7 | 34.4 |
|  | 50% CVF | 47.4 | 56.3 |
|  | 75% CVF | 63.4 | 82.4 |
|  | 90% CVF | 78.3 | 143.3 |

The final drug loads of the two batches were similar and exhibited a high rate of encapsulation efficiency (i.e. >92%). The particle size of the batch prepared with a higher polymer inherent viscosity was larger than that formulated with the lower polymer inherent viscosity, even with a slightly faster emulsification rate. This may be because the dispersed phase of the batch prepared with the higher polymer molecular weight had a higher viscosity than the batch prepared with the lower molecular weight polymer.

Figure 4:
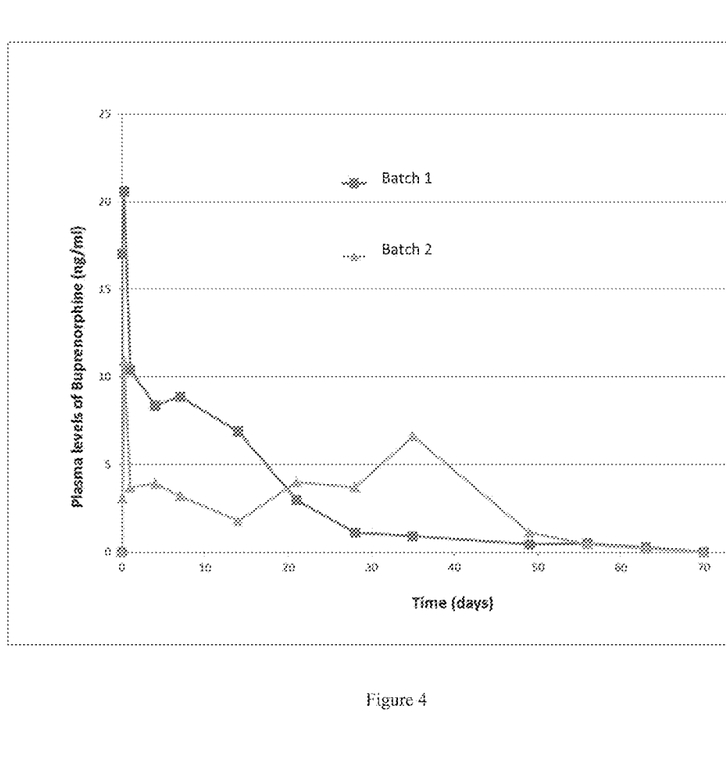
FIG. 4 is a graph of the plasma buprenorphine concentrations in rats given a single administration of microspheres including 15.0 mg buprenorphine/kg and an encapsulating polymer with an inherent viscosity of 0.19 dL/g and 0.34 dL/g, respectively.

Pharmacokinetics of a single administration of both formulations in rats (15 mg buprenorphine/kg) was measured using the prepared microspheres. Plasma buprenorphine concentrations were measured by LC-MS. FIG. 4 shows the plasma buprenorphine levels of the two different batches of prepared microspheres.

As shown in FIG. 4, the polymer molecular weight influenced the initial burst rate and release duration. The initial burst of the batch prepared with the lower molecular weight PLGA was higher, batch 1, about 21 ng/ml as compared to 11 ng/ml for batch 2, and the duration of buprenorphine release increased from about 30 days to about 50 days when the higher molecular weight polymer was utilized.

Example 7

Acid-End Group Versus End-Capped 50:50 PLGA

Buprenorphine (free-base form) was encapsulated into two batches of microspheres using polymers with variations in the end-capping of the polymer chains. The PLGA polymers can either be non-end capped having a free carboxylic acid terminal group, or end-capped, by esterification. For similar polymer molecular weights, carboxylic acid non-end capped polymers are more hydrophilic and thus allow water penetration and eventual hydrolysis and degradation to occur faster compared to the more hydrophobic polymers.

Using 50:50 PLGA polymers with similar molecular weights, microspheres were prepared using both the hydrophilic and hydrophobic polymers. For the first batch using the hydrophilic polymer, a 20 wt % polymer solution was prepared by dissolving 3.75 g of 50:50 PLGA (RG502H commercially available from Evonik with an inherent viscosity=0.19 dL/g) in 15.0 g of a 2:1 mixture of DCM and BzOH. Next, 1.25 g of buprenorphine was added to the polymer solution and mixed to form the dispersed phase.

Next, for the second batch including the hydrophobic polymer, a 13 wt % polymer solution was prepared by dissolving 3.0 g of 50:50 PLGA (RG502S commercially available from Evonik with an inherent viscosity of 0.20 dL/g) in 20.0 g of a 2:1 mixture of DCM and BzOH. Next, 2.0 g of was buprenorphine was added to the polymer solution and mixed to obtain the dispersed phase.

For each batch, a 0.35 wt % PVA continuous phase was prepared by adding PVA to room temperature water and heating and mixing the solution above 70° C. for one hour. After cooling the continuous phase, it was filtered using a 0.2 µm hydrophilic PVDF filter (such as the Durapore membrane from Millipore). The microspheres were prepared using the general method previously described in Example 2. The process parameters for these two batches are given in Table 5, as well as the measured drug load and size distribution of the dried microspheres.

TABLE 6

|  |  | Batch Number | |
| --- | --- | --- | --- |
|  |  | 1 | 2 |
| Buprenorphine |  | Free-base | Free-base |
| Polymer End-Cap |  | Acid end group (Hydrophilic) | End-blocked (Hydrophobic) |
| Mixer Speed (rpm) |  | 2000 | 2000 |
| Target Drug load (wt %) |  | 25 | 40 |
| Dispersed Phase Flow Rate (mL/min) |  | 25 | 25 |
| Continuous Phase Flow Rate (mL/min) |  | 2000 | 2000 |
| Water Dilution Rate (mL/min) |  | 2000 | 2000 |
| Drug Load (wt %) |  | 23.1 | 37.8 |
| Drug encapsulation efficiency, % |  | 92.4 | 94.5 |
| Particle Size, | 10% CVF | 9.5 | 14.2 |
| µm | 25% CVF | 26.7 | 25.8 |
|  | 50% CVF | 47.4 | 37.6 |
|  | 75% CVF | 63.4 | 49.5 |
|  | 90% CVF | 78.3 | 62.9 |

Although the target load was different for the batches, both formulations exhibited a high level of buprenorphine encapsulation efficiency (i.e. >92%). In addition, the size and size distribution of the batches were similar.

Figure 5:
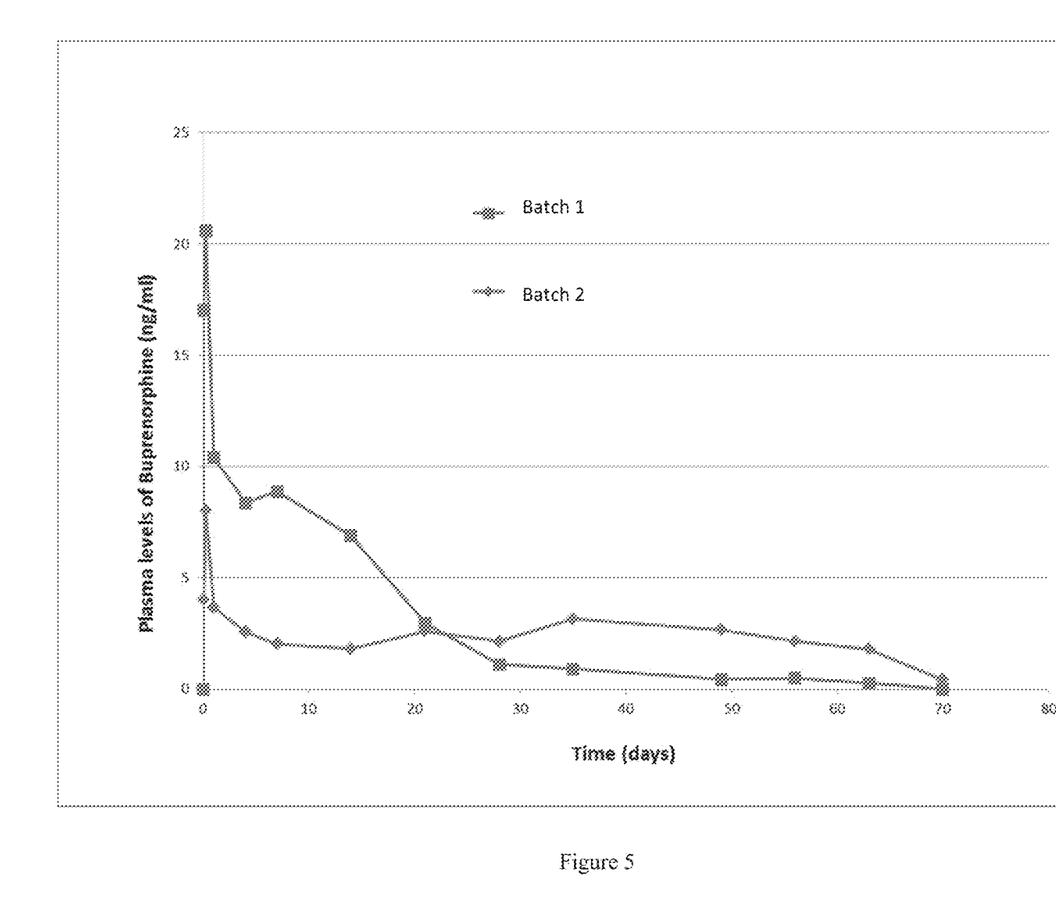
FIG. 5 is a graph of the plasma buprenorphine concentrations in rats given a single administration of microspheres including 15.0 mg buprenorphine/kg and a polymer including an acid end group or an end-blocked polymer, respectively.

Pharmacokinetics of a single administration of both formulations in rats (15 mg buprenorphine/kg) was measured using the prepared microspheres. Plasma buprenorphine concentrations were measured by LC-MS. FIG. 5 shows the plasma buprenorphine levels of the two different batches of prepared microspheres.

As shown in FIG. 5, it is evident that the microsphere batch prepared with the hydrophilic polymer displayed a much higher burst release, about 21 ng/ml, compared to that prepared with the hydrophobic polymer, about 8 ng/ml. This occurred even though the drug load of the hydrophobic polymer batch was much higher (37.8 wt %) compared to the hydrophilic polymer batch (23.1 wt %). In addition, the buprenorphine was substantially released from the batch prepared with the hydrophilic polymer, batch 1, in less than a month, compared to more than two months, but less than three months, for the hydrophobic polymer, batch 2.

Example 8

Long Duration Release Microsphere Formulations

Extended release of buprenorphine over six months to one year may be desired for certain indications. The duration of release of buprenorphine can be controlled by the encapsulating polymer. For the family of PLGA polymers, those made with a higher ratio of lactic acid compared to glycolic acid will provide longer release (for the same molecular weight). In addition, polymers synthesized from polylactic acid only (PLA) provide the longest release durations. Buprenorphine microspheres were prepared with PLGA having a high level of polylactic acid content (i.e. 85 and 100%).

For the first batch, a 8.3 wt % polymer solution was prepared by dissolving 2.5 g of 85:15 PLGA (RG85:15S commercially available from Evonik with inherent viscosity of 0.54 dL/g) in 27.5 g of a 2:1 mixture of DCM and BzOH. Next, 2.5 g of was buprenorphine was added to the polymer solution and dissolved to form the dispersed phase.

For the second batch, a 7.7 wt % polymer solution was prepared by dissolving 2.5 g of 100:0 PLA (R202H, commercially available from Evonik with an inherent viscosity of 0.20 dL/g) in 30 g of a 2:1 mixture of DCM and BzOH. Next, 2.5 g of was buprenorphine was added to the polymer solution to complete the dispersed phase.

For the third batch, a 7.7 wt % polymer solution was prepared by dissolving 2.5 g of 100:0 PLA (R203H, commercially available from Evonik with an inherent viscosity of 0.33 dL/g) in 30 g of a 2:1 mixture of DCM and BzOH. Next, 2.5 g of was buprenorphine was added to the polymer solution and dissolved to complete the dispersed phase.

For each batch, a 0.35 wt % PVA continuous phase was prepared by adding the PVA to room temperature water and heating and mixing the solution above 70° C. for one hour. After cooling the continuous phase, it was filtered using a 0.2 µm hydrophilic PVDF filter (such as the Durapore membrane from Millipore). The microspheres were prepared using the general method previously described in Example 2. The process parameters for these batches are given in Table 7, as well as the measured drug load and size distribution of the dried microspheres.

TABLE 7

|  | Batch Number | | |
| --- | --- | --- | --- |
|  | 1 | 2 | 3 |
| Buprenorphine | Free-base | Free-base | Free-base |
| Co-monomer Ratio | 85:15 | 100:0 | 100:0 |

TABLE 7-continued

| | Batch Number | | |
|---|---|---|---|
| | 1 | 2 | 3 |
| Polymer End-Cap | End-blocked (Hydrophobic) | Acid end (Hydrophilic) | Acid end (Hydrophilic) |
| Polymer $\eta_{inh}$ (dL/g) | 0.54 | 0.20 | 0.33 |
| Mixer Speed (rpm) | 2500 | 2500 | 2000 |
| Target Drug load (wt %) | 50 | 50 | 50 |
| Dispersed Phase Flow Rate (mL/min) | 25 | 25 | 25 |
| Continuous Phase Flow Rate (mL/min) | 2000 | 2000 | 2000 |
| Water Dilution Rate (L/min) | 2 | 2 | 2 |
| Drug Load (wt %) | 45.4 | 46.8 | 46.0 |
| Drug encapsulation effficiency, % | 90.8 | 93.0 | 92.0 |
| Particle Size, 10% CVF | 9.8 | 6.5 | 12.4 |
| μm 25% CVF | 19.4 | 13.1 | 21.5 |
| 50% CVF | 29.9 | 20.3 | 31.3 |
| 75% CVF | 46.2 | 27.1 | 41.9 |
| 90% CVF | 108.1 | 33.5 | 53.2 |

The encapsulation efficiencies for all the batches were greater than 91%. The particle size of the first batch prepared with the 85:15 PLGA polymer was larger due to the higher molecular weight of the polymer resulting high viscosity dispersed phase.

Figure 6:
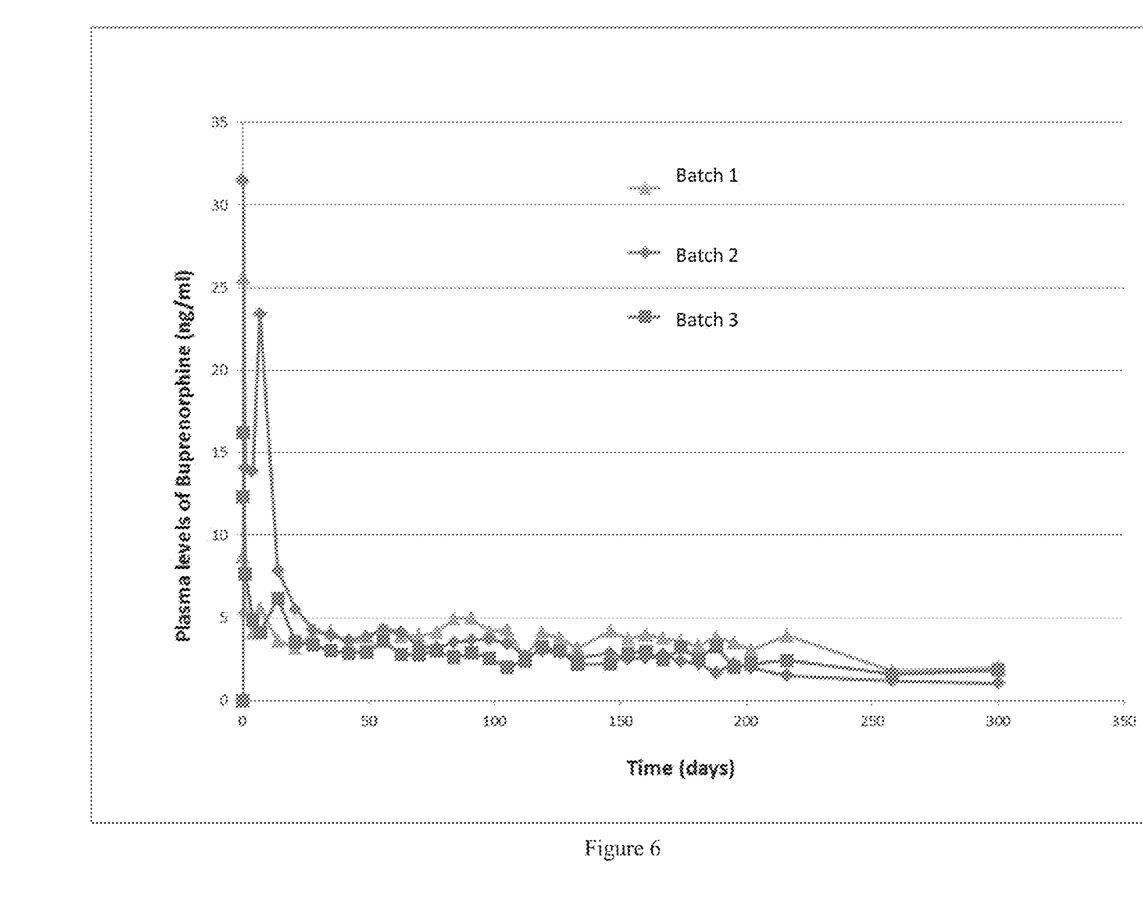
FIG. 6 is a graph of the plasma buprenorphine concentrations in rats given a single administration of microspheres including 100.0 mg buprenorphine/kg and an encapsulating polymer having a ratio of lactic acid to glycolic acid of 85:15 with an inherent viscosity of 0.54 dL/g, a ratio of lactic acid to glycolic acid of 100:0 with an inherent viscosity of 0.20 dL/g, and a ratio of lactic acid to glycolic acid of 100:00 with an inherent viscosity of 0.33 dL/g, respectively.

Pharmacokinetics of a single administration of both formulations in rats (100 mg buprenorphine/kg) was measured using the prepared microspheres. Plasma buprenorphine concentrations were measured by LC-MS. FIG. 6 shows the plasma buprenorphine levels of the three different batches of prepared microspheres. In these batches, the buprenorphine was substantially released over a period of greater than three months, but less than nine months. In addition, after the burst period, the level of buprenorphine was constant over the release profile.

Example 9

Effect of Co-monomer Ratio

The co-monomer ratio also affects the rate of release for encapsulated buprenorphine. For the family of PLGA polymers, those with a higher ratio of lactic acid compared to glycolic acid provided longer release (for the same molecular weight).

Two batches of microspheres were prepared using PLGA with 50:50 and 75:25 co-monomer ratios, but having similar molecular weights. For the first batch, using a 50:50 PLGA co-monomer ratio, a 20 wt % polymer solution was prepared by dissolving 3.75 g of 50:50 PLGA (RG502H commercially available from Evonik with an inherent viscosity of 0.19 dL/g) in 15.0 g of a 2:1 mixture of DCM and BzOH. Next, 1.25 g of was buprenorphine was added to the polymer solution and mixed to form the dispersed phase.

For the second batch using a 75:25 PLGA co-monomer ratio, a 13 wt % polymer solution was prepared by dissolving 3.75 g of 75:25 PLGA (RG752H commercially available from Evonik with an inherent viscosity of 0.18 dL/g) in 25 g of a 2:1 mixture of DCM and BzOH. Next, 1.25 g of buprenorphine was added to the polymer solution to form the dispersed phase.

For each batch, a 0.35 wt % PVA continuous phase was prepared by adding PVA to room temperature water and heating and mixing the continuous phase above 70° C. for one hour. After cooling the continuous phase, it was filtered using a 0.2 μm hydrophilic PVDF filter (such as membrane the Durapore from Millipore). The microspheres were prepared using the general method previously described in Example 2. The process parameters for these two batches are given in Table 8, as well as the measured drug load and size distribution of the dried microspheres.

TABLE 8

| | Batch Number | |
|---|---|---|
| | 1 | 2 |
| Buprenorphine Polymer Co-monomer Ratio | 50:50 | 75:25 |
| Inherent viscosity, dL/g | 0.17 | 0.18 |
| Mixer Speed (rpm) | 2000 | 2400 |
| Target Drug load (wt %) | 25 | 25 |
| Dispersed Phase Flow Rate (mL/min) | 25 | 25 |
| Continuous Phase Flow Rate (mL/min) | 2000 | 2000 |
| Water Dilution Rate (mL/min) | 2000 | 2000 |
| Drug Load (wt %) | 23.1 | 23.5 |
| Drug encapsulation efficiency, % | 92.4 | 94.0 |
| Particle Size, 10% CVF | 9.5 | 7.7 |
| μm 25% CVF | 26.7 | 15.4 |
| 50% CVF | 47.4 | 24.5 |
| 75% CVF | 63.4 | 32.8 |
| 90% CVF | 78.3 | 41.2 |

Both batches displayed similar drug loads, with a high level of encapsulation efficiency (i.e. >92%). The 50:50 PLGA formulation resulted in a larger particle size due to the higher polymer concentration, resulting higher viscosity dispersed phase.

Figure 7:
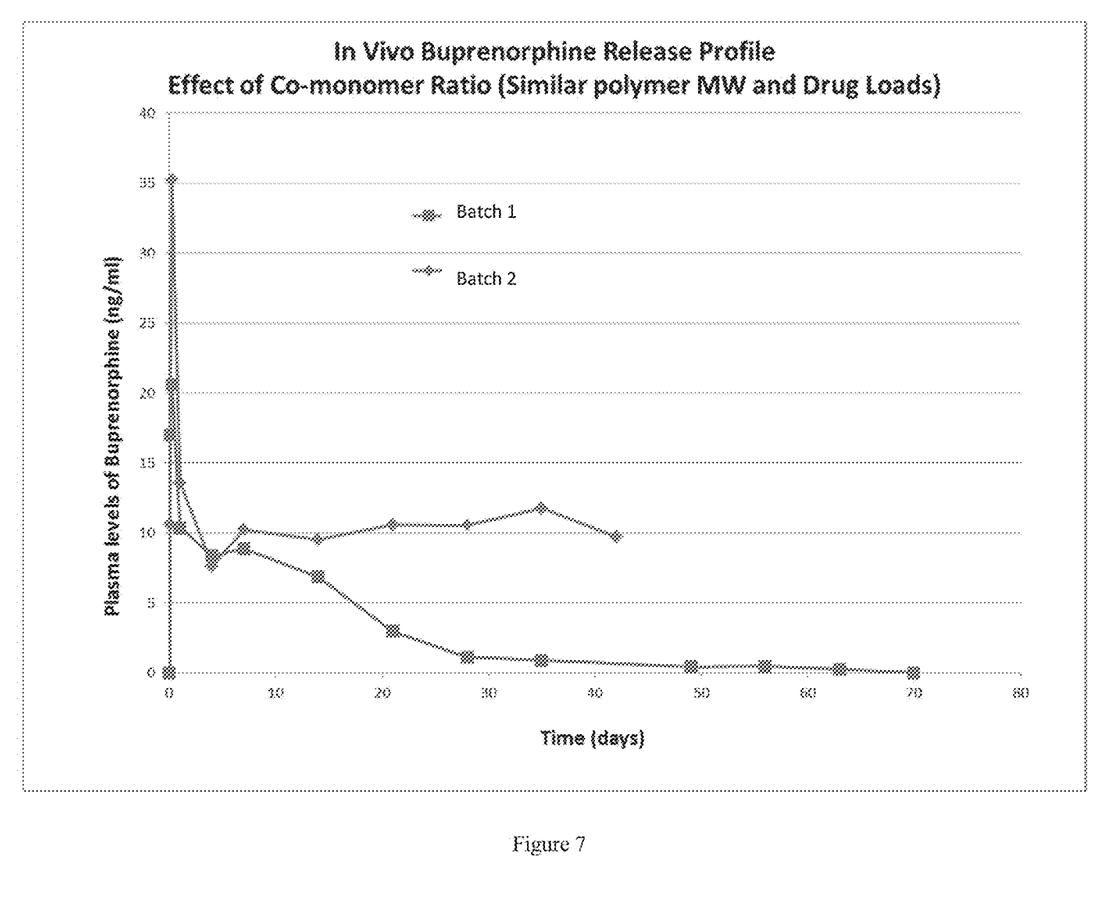
FIG. 7 is a graph of the plasma buprenorphine concentrations in rats given a single administration of microspheres including 15.0 mg buprenorphine/kg and an encapsulating polymer having a 50:50 and 75:25 co-monomer ratio, respectively.

The pharmacokinetics of a single administration of both formulations in rats (15 mg buprenorphine/kg for the 50:50 PLGA and 50 mg/kg buprenorphine/kg for the 75:25 PLGA) was measured using the prepared microspheres. Plasma buprenorphine concentrations were measured by LC-MS. FIG. 7 shows the plasma buprenorphine levels of the two different batches of prepared microspheres.

As shown in FIG. 7, although the batch prepared with the 75:25 PLGA polymer, batch 2, produced a higher burst (mainly due to the higher administered dose), the duration of buprenorphine release was much greater and was not complete at day 42 and still was maintained at a high level. On the other hand, the 50:50 PLGA formulation, batch 1, was exhausted by day 30.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus and method, and illustrative examples shown and described. Accordingly, departures may be made from such details without departing from the spirit or scope of the applicant's general inventive concept.

What is claimed is:

1. A method of making a sustained release microsphere formulation having a high buprenorphine drug load, the method comprising the steps of:
   providing a dispersed phase by mixing an encapsulating polymer, a primary solvent, a pharmaceutically effective amount of buprenorphine free base having a solubility relative to the dispersed phase, and a co-solvent capable of increasing the solubility of the buprenorphine free base relative to the dispersed phase; wherein the ratio of the primary solvent to the co-solvent in the dispersed phase is 2:1 by volume, and wherein the primary solvent is dichloromethane and the co-solvent is benzyl alcohol;

providing a continuous phase comprising an aqueous solution;

mixing the dispersed phase with the continuous phase to form a micro sphere formulation;

wherein the microsphere formulation prepared in the presence of the 2:1 volume ratio of dichloromethane to benzyl alcohol in the dispersed phase has at least a two-fold increase in the release rate of buprenorphine free base compared to a release rate of the microsphere formulation prepared without the addition of benzyl alcohol in the dispersed phase.

2. The method of claim 1, wherein the encapsulating polymer is selected from the group consisting of poly (D,L-lactide-co-glycolide) and poly(L-lactide).

3. The method of claim 1, wherein the buprenorphine free base drug load of the microsphere formulation is about 15% by weight of the microspheres to about 50% by weight of the microspheres.

4. The method of claim 1, wherein the co-solvent is present in an amount of up to 50% by weight of the dispersed phase.

5. The method of claim 1, wherein the increased solubility of the buprenorphine free base relative to the dispersed phase is about 0.02 g/g to about 0.3 g/g.

6. The method of claim 1, wherein the increased solubility of the buprenorphine free base relative to the dispersed phase is about 0.125 g/g to about 0.2 g/g.

7. The method of claim 1, wherein the increased solubility of the buprenorphine free base relative to the dispersed phase is about 0.125 g/g.

8. The method of claim 1, wherein the benzyl alcohol present in the dispersed phase increases the solubility of buprenorphine free base by at least six fold.

9. The method of claim 1, wherein the benzyl alcohol present in the dispersed phase decreases the amount of continuous phase and allows for larger batch sizes to be produced.

* * * * *